US00PP09662P

United States Patent [19]

Slocum

[11] Patent Number: Plant 9,662

[45] Date of Patent: Oct. 15, 1996

[54] WATER LILY PLANT NAME: 'BLACK PRINCESS'

[76] Inventor: Perry D. Slocum, 1831 Leatherman Gap Rd., Franklin, N.C. 28734

[21] Appl. No.: 607,155

[22] Filed: Feb. 26, 1996

[51] Int. Cl.[6] ..... A01H 5/00

[52] U.S. Cl. ..... Plt./87.16

[58] Field of Search ..... Plt./87.16

[56] References Cited

U.S. PATENT DOCUMENTS

P.P. 5,799 11/1986 Slocum ..... Plt./87.16

*Primary Examiner*—James R. Feyrer

[57] ABSTRACT

A novel Water Lily, having red and black peony-shaped blossoms borne approximately 51–76 mm above larger leaves with a first purple then green upper surface and a reddish lower surface with prominent green veins.

5 Drawing Sheets

The present invention relates to a new and distinct variety of Water Lily named Black Princess of the decorative class which was originated by Perry D. Slocum by crossing a Nymphaea, 'Perry's Fire Opal' with a Nymphaea, 'Pamela'.

The primary objective of this breeding was to produce a new and improved Water Lily variety having dark red and black flowers which are hardy and with the flowers extending above the leaves. This objective was achieved along with other desirable improvements as evidenced by the unique combination of characteristics which are outstanding in the new variety and which distinguish it from all other Water Lily varieties by its:

(1) flowers of substantially red outer petals with nearly black inner petals;

(2) round leaves having a usually open sinus, but sometimes closed or partially closed on same plant; and (3) brown stems.

Asexual reproduction of the new variety wich was performed at Franklin, N.C., by tuber division shows that the foregoing characteristics and distinctions come true to form and are established and transmitted through succeeding propagations.

Figure 1:
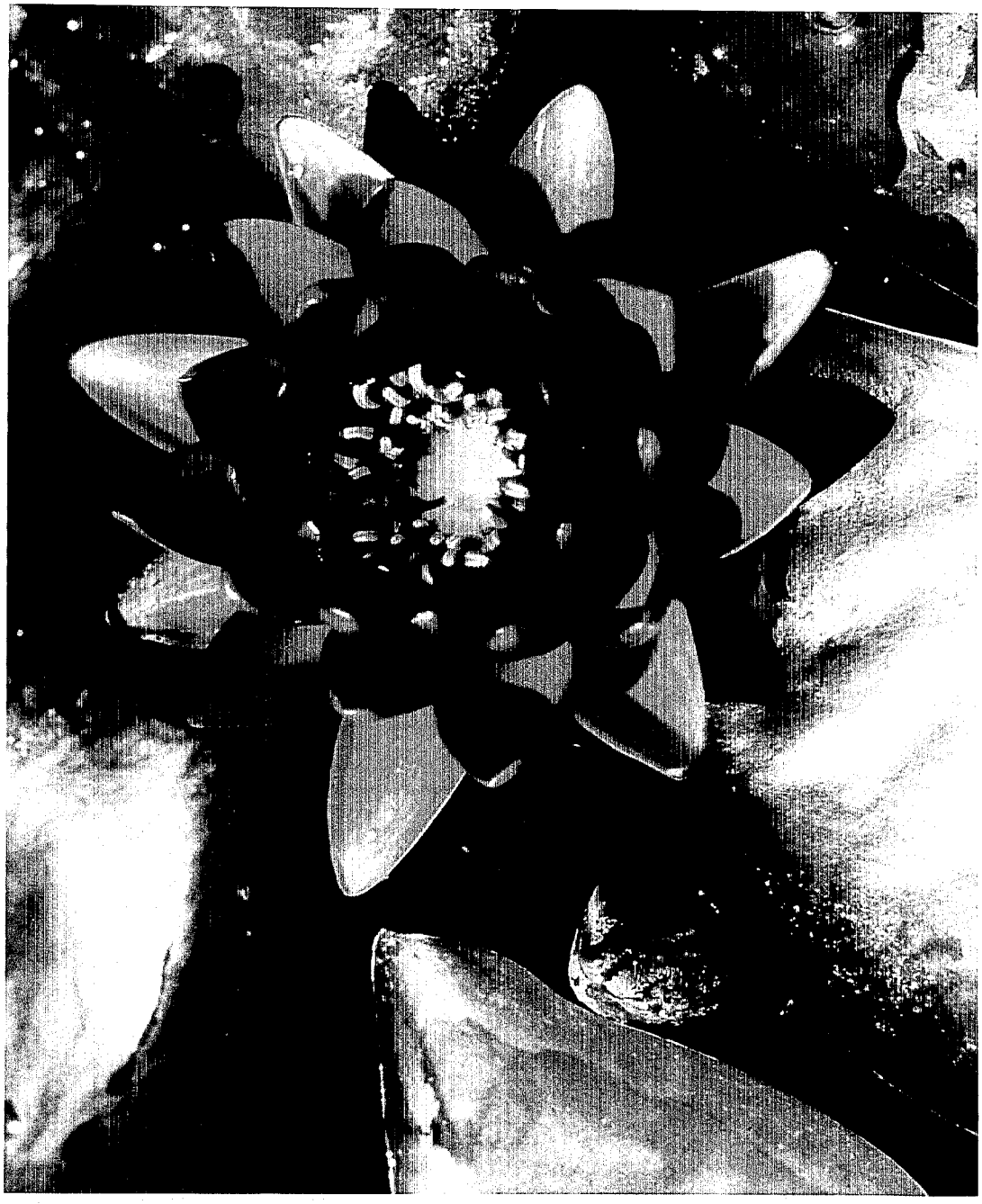
Figure 2:
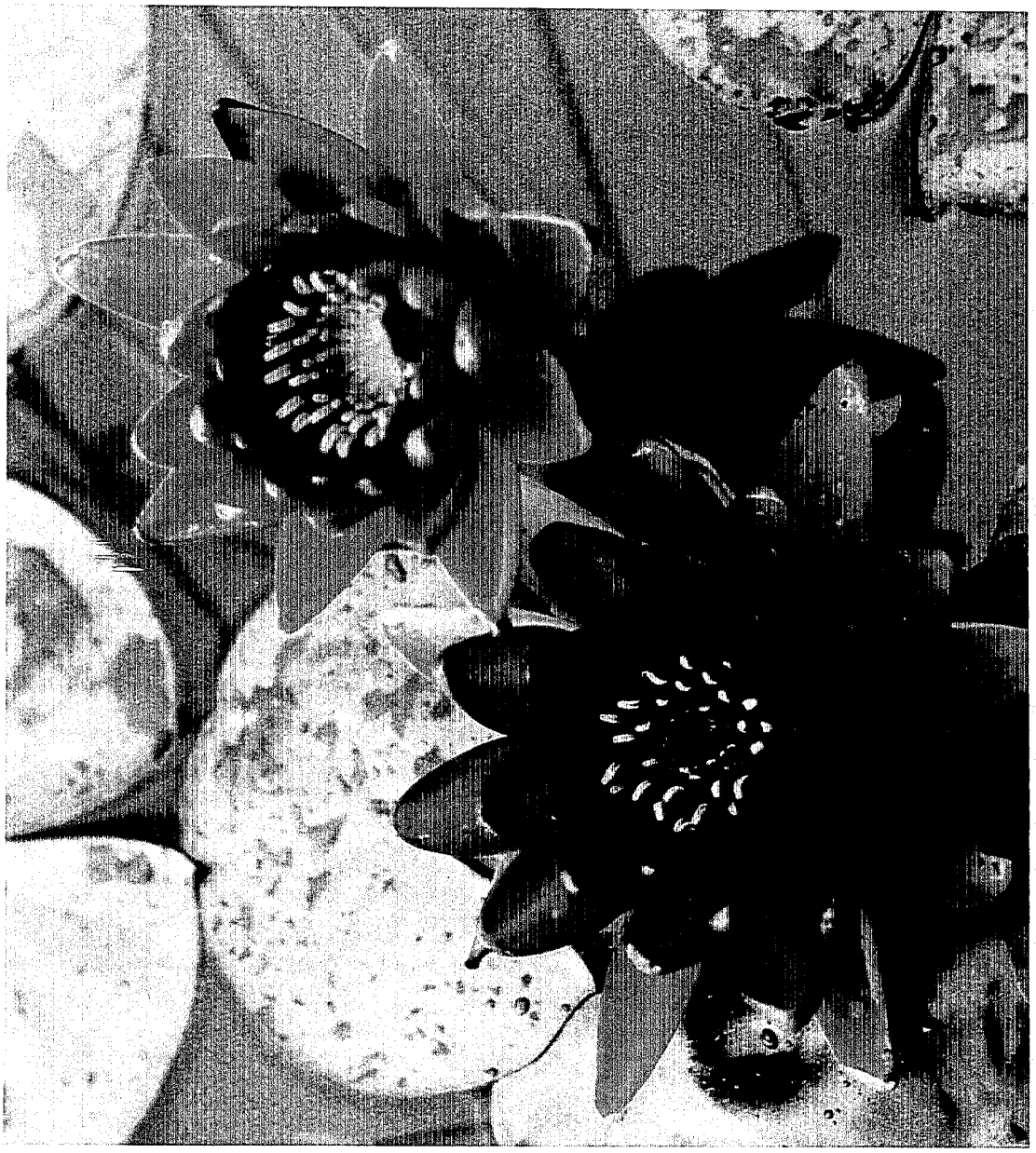
Figure 4:
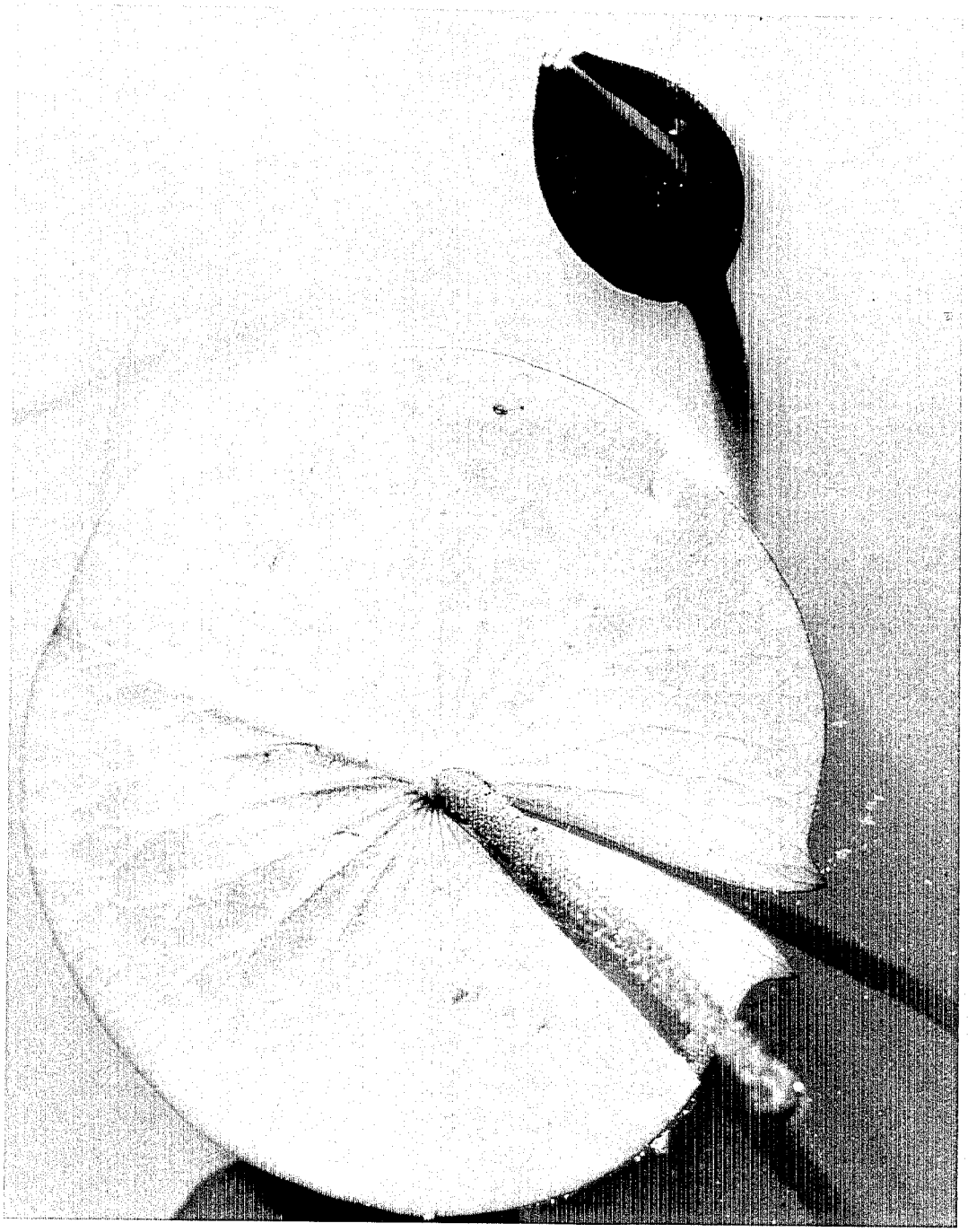
Figure 5:
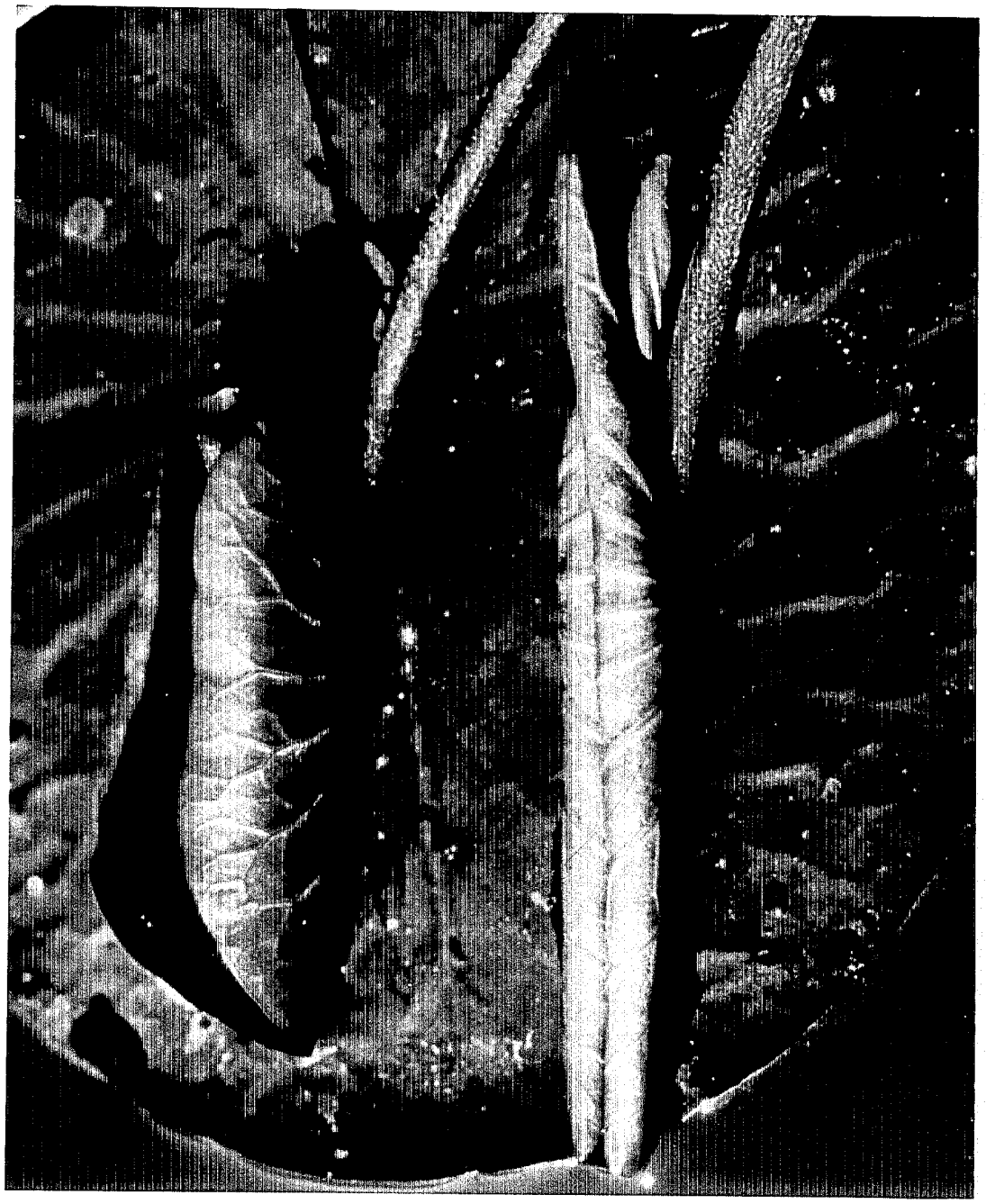

The accompanying photographs (FIGS. 1–5) show typical specimens of the flowers (FIGS. 1 and 2), stem (FIG. 3), bud (FIG. 3) and leaves (FIGS. 4 and 5) of the new Water Lily variety in different stages of development and as depicted in color as nearly true as is reasonably possible to make the same in color photographs of this character.

The following is a detailed description of the new variety, with color terminology in accordance with: Royal Horticultural Society Color Chart, published by The Royal Horticultural Society of London in association with the Flower Council of Holland, Leiden.

Parentage: Seedling.

*Seed parent.*—Nymphaea, variety: 'Perry's Fire Opal'.

*Pollen parent.*—Nymphaea, variety: 'Pamela'.

Classification: Decorative.

Height: Flowers are approximately 51–76 mm above water with 203–228 mm diameter leaves with flowers approximately 127–152 mm in diameter and 51–76 mm above the leaves.

Location where grown and observed: Outdoors in water pools in Franklin, N.C. throughout the year.

Cold resistance: Hardy perennial.

Blooming period: In Franklin, N.C. climatic area, blooming begins in late April and continues through September and early October.

Seed pod: This hybrid does not produce seed pods.

Leaves: Leaves are round and average 203–228 mm with both open and closed sinuses. Tips of lobes have 3–4 mm projections. Upper side of leaf is purple color #187A for a few weeks gradually turning green #147A. Underside of leaf is reddish color #176B with prominent green veins #144A. Stem is brown color #165A.

*Pubescens on peduncle of petiole.*—Both have thick short fuzz.

FLOWER

Figure 3:
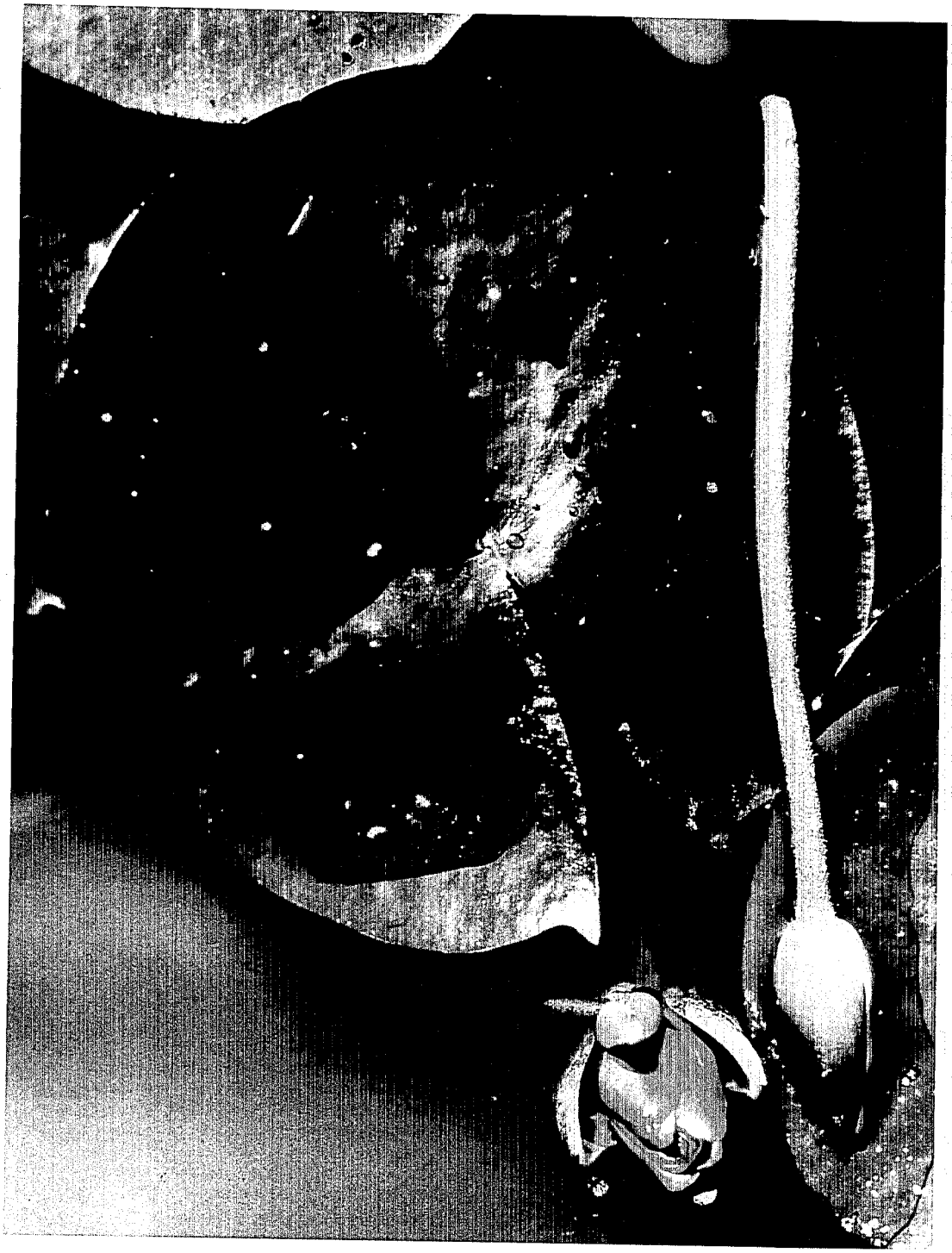

Bud: Color as shown in FIG. 3, upper bud petals have color #187D tips, with #187C body portion with a peduncle of #165A.

*When petals first divide (FIGS. 2 and 3).*—Uppermost petals are #187D. Middle petals approximate #187C with the bottom petals being #187C. This is the outside of the petals.

Bloom:

*Size.*—127–152 mm in diameter.

*Stem.*—Stiff, strong #165A in color.

*Form.*—Cup-shape on first day; peony-shaped on second, third and fourth days.

*Petalage.*—Usually about 36–38.

*Sepals.*—4.

*Stamens.*—81–88.

*Anther.*—81–88.

*Color.*—Center of flower — Center of pistils #13C, at the pistil edge, #23C with anthers #23C and stamens #172D — 172C. Outer petals are between #180B and #183B with the inner petals being #183A to #187A.

Petals:

*Texture.*—Smooth.

Fragrance: Slight, pleasant.

PLANT

Form: All branching of the plant is done under water.

Growth: Medium about 51–76 mm above water.

Foliage:

*Size.*—203–228 mm diameter leaves.

*Quantity.*—Plentiful with about a 1–2 meter spread.

*Color.*—Color of leaves is dark purple #187A for the first few weeks on upper side, gradually turning green #147A and frequently lighter to 147D. The underside of a new rolled up leaf is buffy-brown #173D soon becoming reddish #176B with prominent green veins #144A which usually appear lighter in photographs.

*Texture.*—Smooth. Petiole (stem) brown #165A, hairy.

I claim:

1. A new and distinct variety of Water Lily plant substantially as herein shown and described.

* * * * *